United States Patent
Kriete et al.

(10) Patent No.: US 12,310,645 B1
(45) Date of Patent: May 27, 2025

(54) PEDICLE SCREW REMOVER

(71) Applicant: Deannalyn, Inc., Clermont, FL (US)

(72) Inventors: John Kriete, Clermont, FL (US); Deanna Kriete, Clermont, FL (US)

(73) Assignee: DEANNALYN, INC., Clermont, FL (US)

( * ) Notice: Subject to any disclaimer, the term of this patent is extended or adjusted under 35 U.S.C. 154(b) by 0 days.

(21) Appl. No.: 18/052,408

(22) Filed: Nov. 3, 2022

Related U.S. Application Data

(60) Provisional application No. 63/275,540, filed on Nov. 4, 2021.

(51) Int. Cl.
*A61B 17/88* (2006.01)

(52) U.S. Cl.
CPC .................. *A61B 17/8883* (2013.01)

(58) Field of Classification Search
CPC .................. A61B 17/888; A61B 17/8888
See application file for complete search history.

(56) References Cited

U.S. PATENT DOCUMENTS

| | | | | |
|---|---|---|---|---|
| 5,090,102 A | * | 2/1992 | Lovell | B25B 27/06 29/255 |
| 6,286,401 B1 | * | 9/2001 | Hajianpour | B25B 23/108 81/453 |
| 2005/0033307 A1 | * | 2/2005 | Cook | A61B 17/8888 606/104 |
| 2021/0322078 A1 | * | 10/2021 | Scherrer | A61B 17/8615 |

* cited by examiner

*Primary Examiner* — Nicholas W Woodall
(74) *Attorney, Agent, or Firm* — ALLEN, DYER, DOPPELT + GILCHRIST, P.A.

(57) ABSTRACT

A pedicle screw remover includes a body, a driver head, forward and rear driver rods and a handle. The driver head is outwardly expandable via advancement of the driver rods to engage a pedicle screw and socket. Once engaged, the entire device is rotatable via the handle to withdraw the engaged screw and socket. The driver head is removable from the body and replaceable with other driver heads.

18 Claims, 4 Drawing Sheets

PEDICLE SCREW REMOVER

CROSS-REFERENCE TO RELATED APPLICATION

This application claims the benefit of U.S. Provisional Patent Application Ser. No. 63/275,540, filed on Nov. 4, 2021, the contents of which are herein incorporated by reference in their entirety.

FIELD OF THE INVENTION

The present invention relates to removing implanted medical hardware, and, more particularly, to devices for removing pedicle screws.

BACKGROUND OF THE INVENTION

While some implanted medical hardware may remain in place for the life of the patient, it is sometimes the case that removal of some or all previously implanted hardware may be necessary in a subsequent procedure. One example of this is the pedicle screws used in spinal fusion procedures. Hardware removal, particularly when done an appreciable time after the original implantation and/or by a different practitioner, can present problems beyond those risks normally attendant on all surgery.

For instance, pedicle screws are normally inserted using a driver with a custom head for engagement with a hex socket on the distal end of the screw. Complicating matters further, as most pedicle screws are designed to be poly-axial, the screw head is spherical and pivotably seated within a socket (sometimes called a tulip). Even where the same custom head used to install the screw is available for removal, engagement of the screw head within the housing can be challenging. Where, as is frequently the case after a lapse of years and/or change of doctors, the custom head is not available, removal of the screw and socket becomes even more challenging.

Various devices have been developed to try to address this problem. For example, the present inventors developed the removal devices disclosed in U.S. Pat. No. 10,349,985, the contents of which are herein incorporated by reference in their entirety. The '985 Patent devices are operable to engage the socket while also effectively locking the screw head to the socket. Consequently, rotation of the socket with the device will result in withdrawal of both socket and screw. While removal devices as disclosed in the '985 patent are useful, further improvements are possible.

SUMMARY OF THE INVENTION

In view of the foregoing, it is an object of the present invention to provide an improved pedicle screw remover and related methods.

A pedicle screw remover includes a body, a driver head, forward and rear driver rods and a handle. The body defines a body internal passage extending between proximal and distal body ends, female threads being formed at the distal body end. The driver head defining a head internal passage extending between proximal and distal head ends, socket arms being formed at the proximal head end separated by a slot connected with the head internal passage, the distal head end being removably attached to the proximal body end such that the head internal passage connects with the body internal passage.

The forward driver rod extends between proximal and distal forward rod ends, the forward driver rod being slidably received within the body and head internal passages with the proximal forward rod end extending into the slot. The rear driver rod extends between proximal and distal rear rod ends, male threads on the rear driver rod engaging the female threads at the distal body end and the proximal rear rod end being rotatably coupled to the distal forward rod end in the body internal passage such that threading the rear driver rod further into the body internal passage advances the proximal forward rod end further into the slot resulting in outward movement of the socket arms. The handle coupled externally to the distal body end and operable to rotate the entire pedicle screw remover.

These and other objects, aspects and advantages of the present invention will be better appreciated in view of the drawings and following detailed description of preferred embodiments.

DETAILED DESCRIPTION OF PREFERRED EMBODIMENTS

Figure 1:
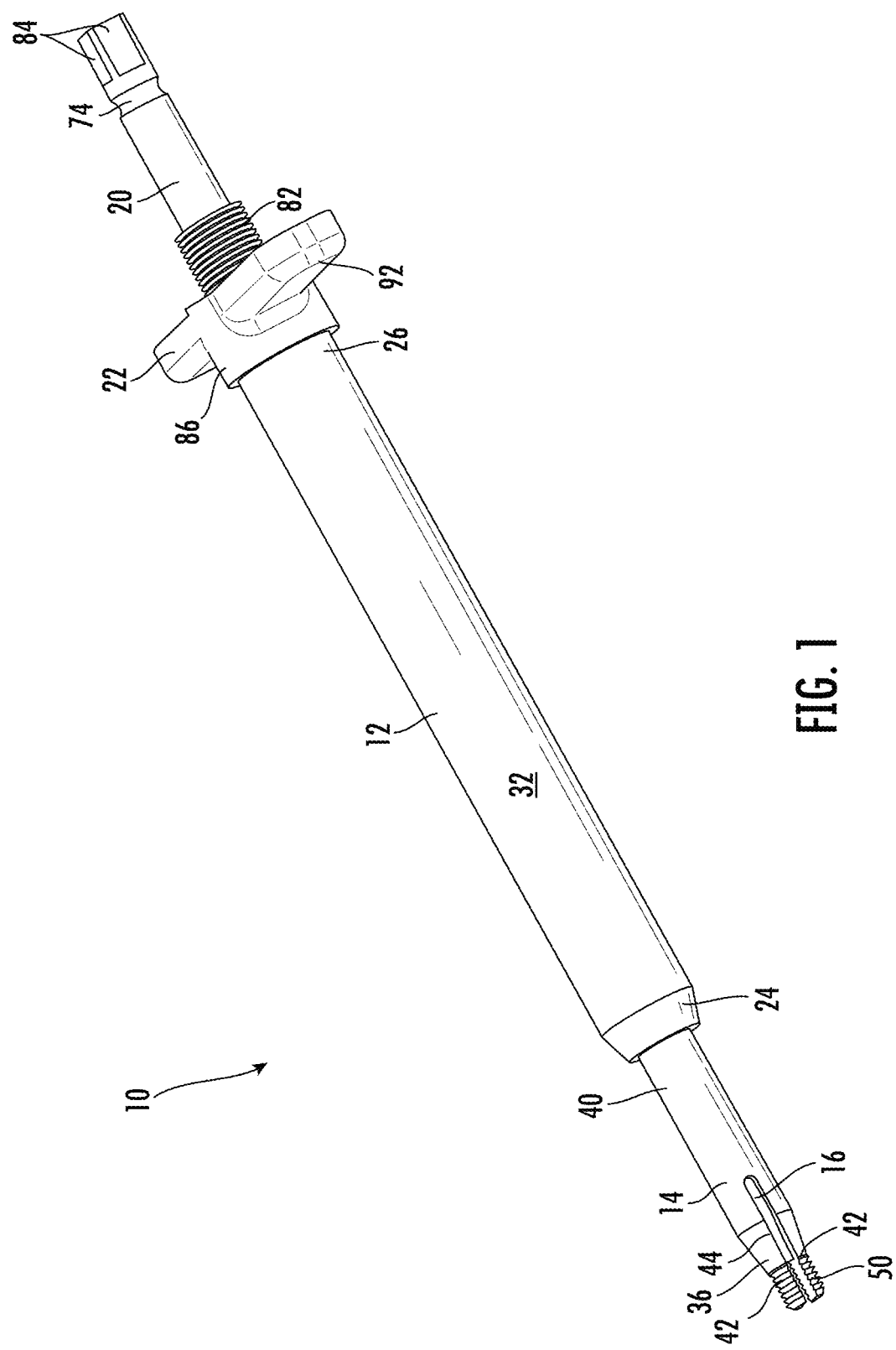
FIG. 1 is a perspective view of a pedicle screw remover, according to an embodiment of the present invention.
Figure 2:
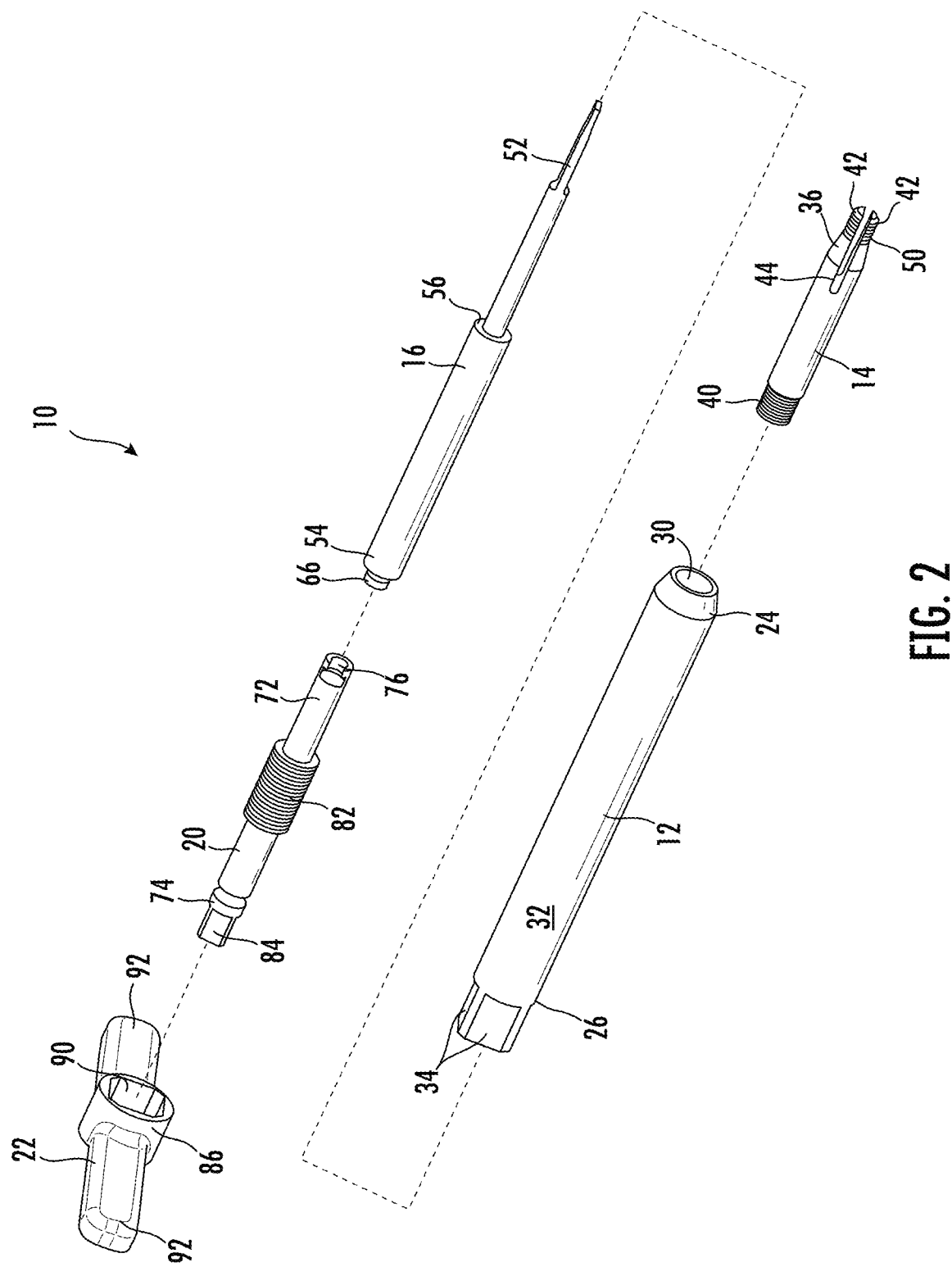
FIG. 2 is an exploded perspective view of the pedicle screw remover of FIG. 1.
Figure 3:
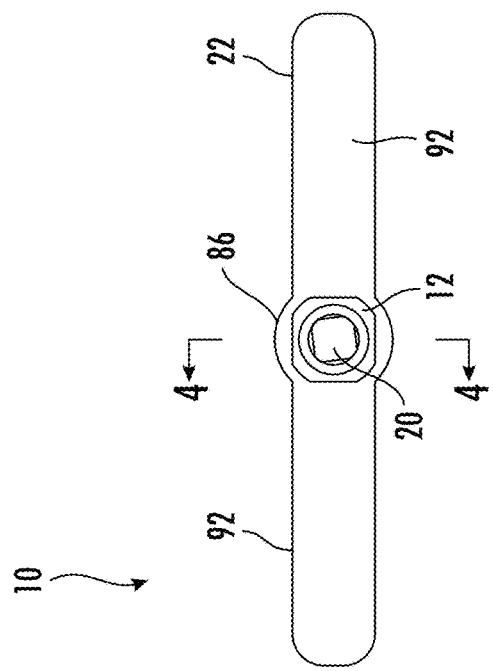
FIG. 3 is an end view of the pedicle screw remover of FIG. 1.
Figure 4:
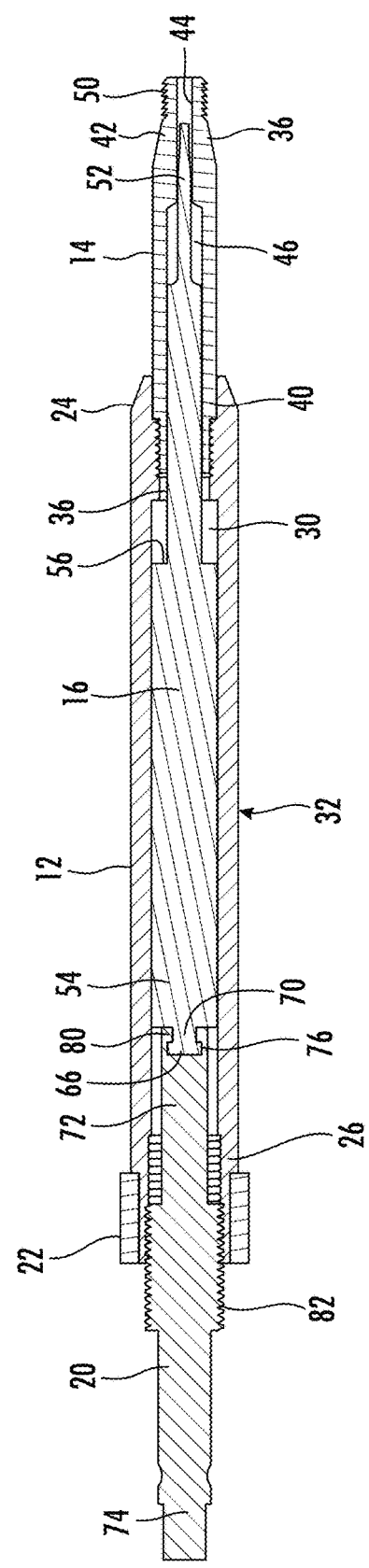
FIG. 4 is a cross-sectional view taken along line 4-4 of FIG. 3.

According to an embodiment of the present invention, referring to FIGS. 1-4, a pedicle screw remover 10 includes a body 12, a driver head 14, forward and rear driver rods 16, 20 and a handle 22. The driver head 14 is outwardly expandable via advancement of the driver rods 16, 20 to engage a pedicle screw and socket. Once engaged, the entire device 10 is rotatable via the handle 22 to withdraw the engaged screw and socket.

The body 12 extends between proximal and distal ends 24, 26 and defines an internal passage 30 therebetween. Toward the proximal end 24, an outer surface 32 of the body 12 preferably tapers inwardly. Engagement surfaces 34 are formed in the outer surface 32 at the distal end 26 to rotationally couple the body 12 to the handle 22. The internal passage 30 is preferably substantially cylindrical and threaded at the proximal and distal ends 24, 26 to receive the driver head 14 and the rear driver rod 20, respectively. Additionally, a restriction 36 is formed within the passage 30 to delimit travel of the forward driver rod 16.

The driver head 14 extends between proximal and distal ends 36, 40. Socket arms 42 are formed at the proximal end 36 separated by a slot 44. An internal passage 46 is defined within the driver head from the distal end 40 extending to the slot 44 for accommodating the forward driver rod 16. The distal end 40 is externally threaded for engagement with the threads of the internal passage 30 at the proximal end 24 of the body 12.

The socket arms 42 are able to flex outwards when engaged by the forward driver rod 16. Ridges 50 are formed on outer sides of the ends of the socket arms 42 to better engage the interior of a pedicle screw socket.

Figure 5A:
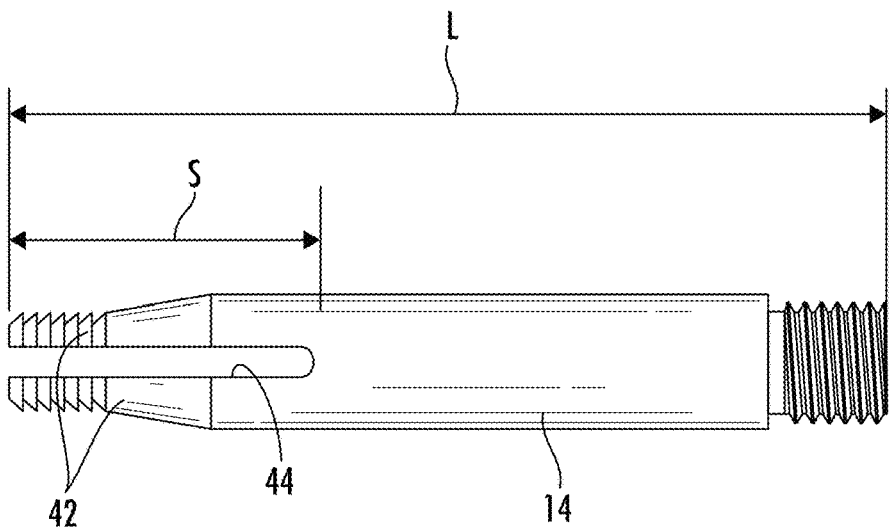
FIGS. 5A and 5B are side views of alternate driver heads of the pedicle screw remover of FIG. 1.
Figure 5B:
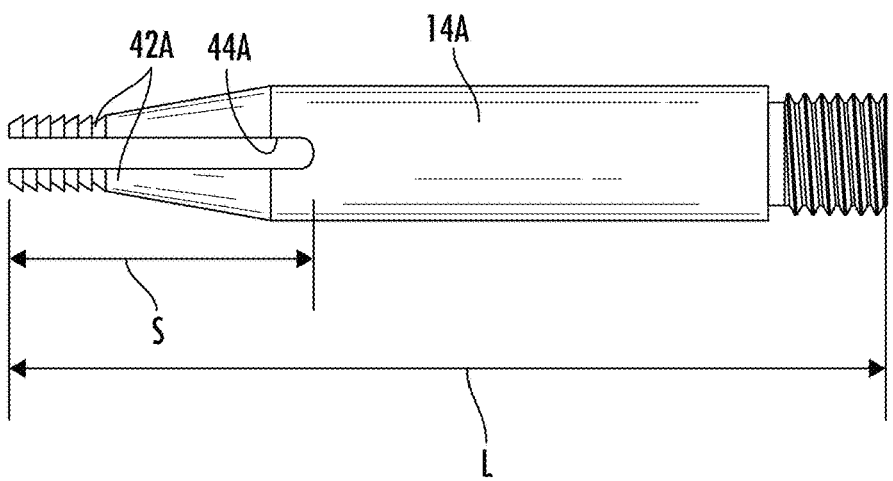

Referring to FIGS. 5A and 5B, the driver head 14 is advantageously readily interchangeable with one or more other driver head 14A, substantially identical except for differently dimensioned socket arms 42, 42A. Preferably, an overall length L and a slot 44, 44A length S are identical such that the driver heads 14, 14A are compatible with the same forward driver rod 16. In addition to allowing the device 10 to more readily accommodate different socket dimensions, this configuration facilitates replacement of worn or broken driver heads 14, 14A.

Figure 6:
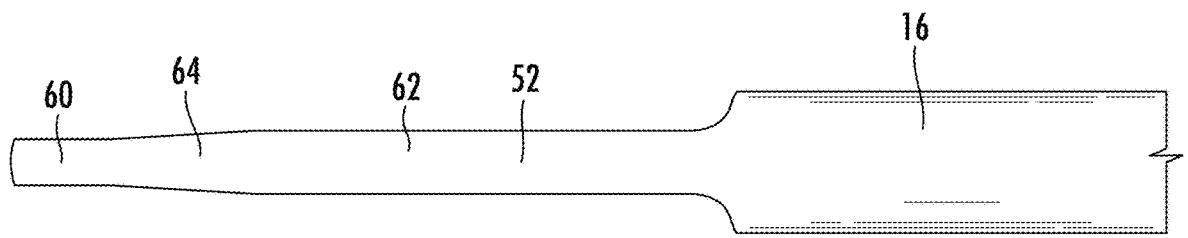
FIG. 6 is an enlarged view of a proximal end of a forward driver rod of the pedicle screw remover of FIG. 1.

Referring also to FIG. 6, the forward driver rod 16 extends between proximal and distal ends 52, 54. Most of the forward driver rod 16 is cylindrical so as to be closely accommodated within the internal passage 30 of the body. However, the diameter of the forward driver rod 16 decreases at a shoulder 56, which engages the restriction 36 while allowing the proximal end 52 to pass through.

At the proximal end 52, the forward driver rod 16 transitions to a generally flat shape for better accommodation within the slot 44. Preferably, the generally flat shape increases slightly in thickness moving rearwardly. Most preferably, the forward driver rod 16 transitions from a first flat section 60 to a thicker second flat section 62 via a tapered section 64. The thickness of the first flat section 60 is advantageously less than a thickness of the slot 44 where it meets the internal passage 46, while the second flat section 62 is approximately equal to the slot thickness at this point. Consequently, advancing the second flat section 62 into the slot will ensure that the socket arms 42 are fully flexed outward.

The distal end 54 of the forward driver rod 16 includes a button 66 with a decreased diameter post 70. The button 66 couples the distal end 54 of the forward driver 16 to the rear driver rod 20. Releasably coupling the forward driver rod 16 to the rear driver rod 20 facilitates independent replacement of the forward driver rod 16 if it becomes worn or broken, or if use of a differently configured forward driver rod 16 were desired.

The rear driver rod 20 extends between proximal and distal ends 72, 74. A necked slot 76 is formed in the proximal end 72 such that the button 66 of the forward driver rod 16 can be inserted sideways into the proximal end 72 of the rear driver rod 20 with the decreased diameter post 70 of the button 66 extending through the necked portion 80 of the slot 76. Engagement surfaces 84 are formed on the distal end 74 to allow engagement of a handle or other means for facilitating rotation of the rear driver rod 20.

Between the proximal and distal ends 72, 74, external threads 82 are formed around the rear driver rod 20 to engage the threads in internal passage 30 at the distal end 26 of the body 12. With the threads of the body 12 and rod 20 engaged, rotation of the read driver rod 20 will result in translational movement therebetween. The coupling between the button 66 and the necked slot 76 allows this translational movement to be transferred to the forward driver rod 16 without transferring the rotational movement.

The handle 22 has a hub 86 defining a passage 90 configured to be complementary with the engagement surfaces 34 on the outer surface 32 of the body 12. Arms 92 extending outwardly from the handle 22 allow a user to apply greater torque to rotate the pedicle screw remover 10 to extract a pedicle screw and socket.

In use, a suitable driver head 14 (or 14A) is selected and its distal end 40 is threaded into the internal passage 30 at the proximal end 26 of the body. The forward driver and rear driver rods 16, 20 are coupled via the button 66 and necked slot 76 and inserted into the internal passage 30 from distal end 26 of the body 12, with the external threads 82 partially threaded into the internal passage 30 threads so the first flat section 60 is at least partially extending into the slot 44 of the driver head 14 (14A).

The user then inserts the socket arms 42 (42A) of the driver head 14 (14A) into the socket of the pedicle screw to be removed. The distal end 74 of the rear driver rod 20 is then rotated to advance the front and rear driver rods 16, 20 until the distal end 54 of the forward driver rod 16 is firmly engaging the head of the pedicle screw and the socket arms 42 (42A) are firmly engaging the inner walls of the socket. This effectively locks the socket and pedicle screw together.

The handle 22 is then placed over the distal end 26 of the body 12 to engage the passage 90 with the engagement surfaces 34. The user then rotates the handle 22 to withdraw the socket and pedicle screw. The handle 22 could be mounted to the body 12 at any time, although leaving it off initially can help improve visualization and manipulation when engaging the pedicle screw and socket.

In general, the foregoing description is provided for exemplary and illustrative purposes; the present invention is not necessarily limited thereto. Rather, those skilled in the art will appreciate that additional modifications, as well as adaptations for particular circumstances, will fall within the scope of the invention as herein shown and described and the claims appended hereto.

What is claimed is:

1. A pedicle screw remover comprising:
   a body defining a body internal passage extending between proximal and distal body ends, female threads being formed at the distal body end;
   a driver head defining a head internal passage extending between proximal and distal head ends, socket arms being formed at the proximal head end separated by a slot connected with the head internal passage and a plurality of longitudinally spaced ridges extending circumferentially around outer sides of the socket arms, the distal head end being removably attached to the proximal body end such that the head internal passage connects with the body internal passage;
   a forward driver rod extending between proximal and distal forward rod ends, the forward driver rod being slidably received within the body and head internal passages with the proximal forward rod end extending into the slot;
   a rear driver rod extending between proximal and distal rear rod ends, male threads on the rear driver rod engaging the female threads at the distal body end and the proximal rear rod end being rotatably coupled to the distal forward rod end in the body internal passage such that threading the rear driver rod further into the body internal passage advances the proximal forward rod end further into the slot resulting in outward movement of the socket arms; and
   a handle coupled externally to the distal body end and operable to rotate the entire pedicle screw remover.

2. The pedicle screw remover of claim 1, wherein an outer surface of the proximal body end tapers inwardly.

3. The pedicle screw remover of claim 1, wherein the body internal passageway is substantially cylindrical.

4. The pedicle screw remover of claim 1, wherein the body has a restriction formed in the body internal passageway to delimit travel of the forward driver rod.

5. The pedicle screw remover of claim 4, wherein the forward driver rod has a shoulder configured to engage the restriction of the body internal passageway while allowing the proximal end of the forward driving rod to pass through the proximal end of the body.

6. The pedicle screw remover of claim 1, wherein the forward driver rod transitions to a substantially flat shape at the proximal forward rod end.

7. The pedicle screw remover of claim 1, wherein the forward driver rod tapers from a first flat section to a second flat section, wherein a thickness of the first flat section is less than a thickness of the slot, and a thickness of the second flat section is at least the same thickness of the slot.

8. The pedicle screw remover of claim 1, wherein the distal forward driver rod end has a button configured to releasably couple to the proximal rear driver rod end.

9. The pedicle screw remover of claim 8, wherein the proximal rear driver rod end has a necked slot having a necked slot for receiving the button of the distal forward driver rod end.

10. The pedicle screw remover of claim 1, wherein the handle comprises a hub engaged with the body, and a plurality of outwardly extending arms configured to apply torque to rotate the pedicle screw remover.

11. A pedicle screw remover comprising:
a body defining a body internal passage extending between proximal and distal body ends, female threads being formed at the distal body end;
a driver head defining a head internal passage extending between proximal and distal head ends, socket arms being formed at the proximal head end separated by a slot connected with the head internal passage and a plurality of longitudinally spaced ridges extending circumferentially around outer sides of the socket arms, the distal head end being removably attached to the proximal body end such that the head internal passage connects with the body internal passage; and
a forward driver rod extending between proximal and distal forward rod ends, the forward driver rod being slidably received within the body and head internal passages with the proximal forward rod end extending into the slot;
wherein an outer surface of the proximal body end tapers inwardly.

12. The pedicle screw remover of claim 11, further comprising a rear driver rod extending between proximal and distal rear rod ends, male threads on the rear driver rod engaging the female threads at the distal body end and the proximal rear rod end being rotatably coupled to the distal forward rod end in the body internal passage such that threading the rear driver rod further into the body internal passage advances the proximal forward rod end further into the slot resulting in outward movement of the socket arms.

13. The pedicle screw remover of claim 12, further comprising a handle coupled externally to the distal body end and operable to rotate the entire pedicle screw remover.

14. The pedicle screw remover of claim 12, wherein the distal forward driver rod end has a button configured to releasably couple to the proximal rear driver rod end.

15. The pedicle screw remover of claim 14, wherein the proximal rear driver rod end has a necked slot having a necked slot for receiving the button of the distal forward driver rod end.

16. The pedicle screw remover of claim 11, wherein the body has a restriction formed in the body internal passageway to delimit travel of the forward driver rod.

17. The pedicle screw remover of claim 16, wherein the forward driver rod has a shoulder configured to engage the restriction of the body internal passageway while allowing the proximal end of the forward driving rod to pass through the proximal end of the body.

18. The pedicle screw remover of claim 11, wherein the forward driver rod tapers from a first flat section to a second flat section, wherein a thickness of the first flat section is less than a thickness of the slot, and a thickness of the second flat section is at least the same thickness of the slot.

\* \* \* \* \*